US00PP35424P2

(12) United States Plant Patent
Boosey

(10) Patent No.: US PP35,424 P2
(45) Date of Patent: Oct. 17, 2023

(54) ***OLEARIA* PLANT NAMED 'ARKPAP'**

(50) Latin Name: *Olearia phlogopappa*
Varietal Denomination: ARKPAP

(71) Applicant: Paul Boosey, Hampshire (GB)

(72) Inventor: Paul Boosey, Hampshire (GB)

(73) Assignee: COUNTY PARK NURSERY, LTD., Hampshire (GB)

( * ) Notice: Subject to any disclaimer, the term of this patent is extended or adjusted under 35 U.S.C. 154(b) by 0 days.

(21) Appl. No.: 18/104,335

(22) Filed: Feb. 1, 2023

Related U.S. Application Data

(60) Provisional application No. 63/315,148, filed on Mar. 1, 2022.

(51) Int. Cl.
*A01H 5/02* (2018.01)
*A01H 6/14* (2018.01)

(52) U.S. Cl.
USPC ..... Plt./226

(58) Field of Classification Search
USPC ..... Plt./226, 263.1
CPC ..... A01H 5/02; A01H 5/00; A01H 6/00
See application file for complete search history.

*Primary Examiner* — June Hwu
(74) *Attorney, Agent, or Firm* — Penny J. Aguirre

(57) ABSTRACT

A new cultivar of *Olearia* plant named 'ARKPAP' that is characterized by its fragrant foliage, its rigid plant structure, its short stem internodes, its small leaves, its large flowers, its long flowering period.

3 Drawing Sheets

Botanical classification: *Olearia phlogopappa.*
Variety denomination: 'ARKPAP'.

BACKGROUND OF THE INVENTION

The present invention relates to a new and distinct cultivar of *Olearia,* botanically known as *Olearia phlogopappa* 'ARKPAP', and will be referred to hereafter by its cultivar name 'ARKPAP'. 'ARKPAP' is a new evergreen shrub suitable for landscape plantings.

'ARKPAP' was discovered by the Inventor as a chance seedling that was growing in a container at a nursery in Hornchurch, Essex, The United Kingdom in July of 2011. The container was located in a container block that had planted with seedlings of unnamed and unpatented plants of *Olearia phlogopappa.* The exact seed parent in unknown.

The new cultivar was first asexually propagated by stem cuttings by the Inventor in Hornchurch, Essex, The United Kingdom in 2015. Asexual propagation by stem cuttings and division has determined that the characteristics of this cultivar are stable and are reproduced true to type in successive generations.

SUMMARY OF THE INVENTION

The following traits have been repeatedly observed and represent the characteristics of the new *Olearia.* These attributes in combination distinguish 'ARKPAP' as a unique cultivar of *Olearia.*

1. 'ARKPAP' exhibits fragrant foliage.
2. 'ARKPAP' exhibits a rigid plant structure.
3. 'ARKPAP' exhibits short stem internodes.
4. 'ARKPAP' exhibits small leaves.
5. 'ARKPAP' exhibits large flowers.
6. 'ARKPAP' exhibits a long flowering period.

The plants of *Olearia phlogopappa* growing in the container block that 'ARKPAP' was discovered in all differ from 'ARKPAP' in having more open and less rigid plant structures, larger leaf sizes, longer stem internodes, flowers that are smaller in size, and shorter flowering periods. 'ARKPAP' can be most closely compared to typical plants of *Olearia* x *scillionensis, Olearia phlogopappa* 'Combers Pink' (not patented) and *Olearia* x *scillionensis* 'Master Michael' (not patented). Plants of *Olearia* x *scillionensis* differs from 'ARKPAP' in having a larger plant size, leaves that are larger in size, a less rigid plant structure, flowers that are larger in size, and in producing less flowers. 'Combers Pink' and 'Master Michael' both differ from 'ARKPAP' in having leaves that are larger in size, a less rigid plant structure, flowers that are different in color, and a less floriferous blooming habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. The Applicant claims a prior art exemption under 35 U.S.C. 102(b)(1) for disclosures and/or sales that fall within a one-year grace period to the filing date. Disclosures include website listings by RHS plants, Crocus, Waitrose Gardens, Gardeners Dream, ebay, Morton Nursery, NumaOnline, Globe Planter, Garden Center Finder, Shoot Gardening, Anglian Gardener, Genesis Plant Marketing and Planteria.

BRIEF DESCRIPTION OF THE DRAWINGS

The accompanying color photographs were photographed in The Netherlands for this botany study. The photographs illustrate the overall appearance and distinct characteristics of 2-year-old plants of the new *Olearia* as grown in a greenhouse in a 23-cm container in Essex, The United Kingdom.

The photograph in FIG. 1 provides a view of the plant habit of 'ARKPAP' in bloom.

Figure 1:
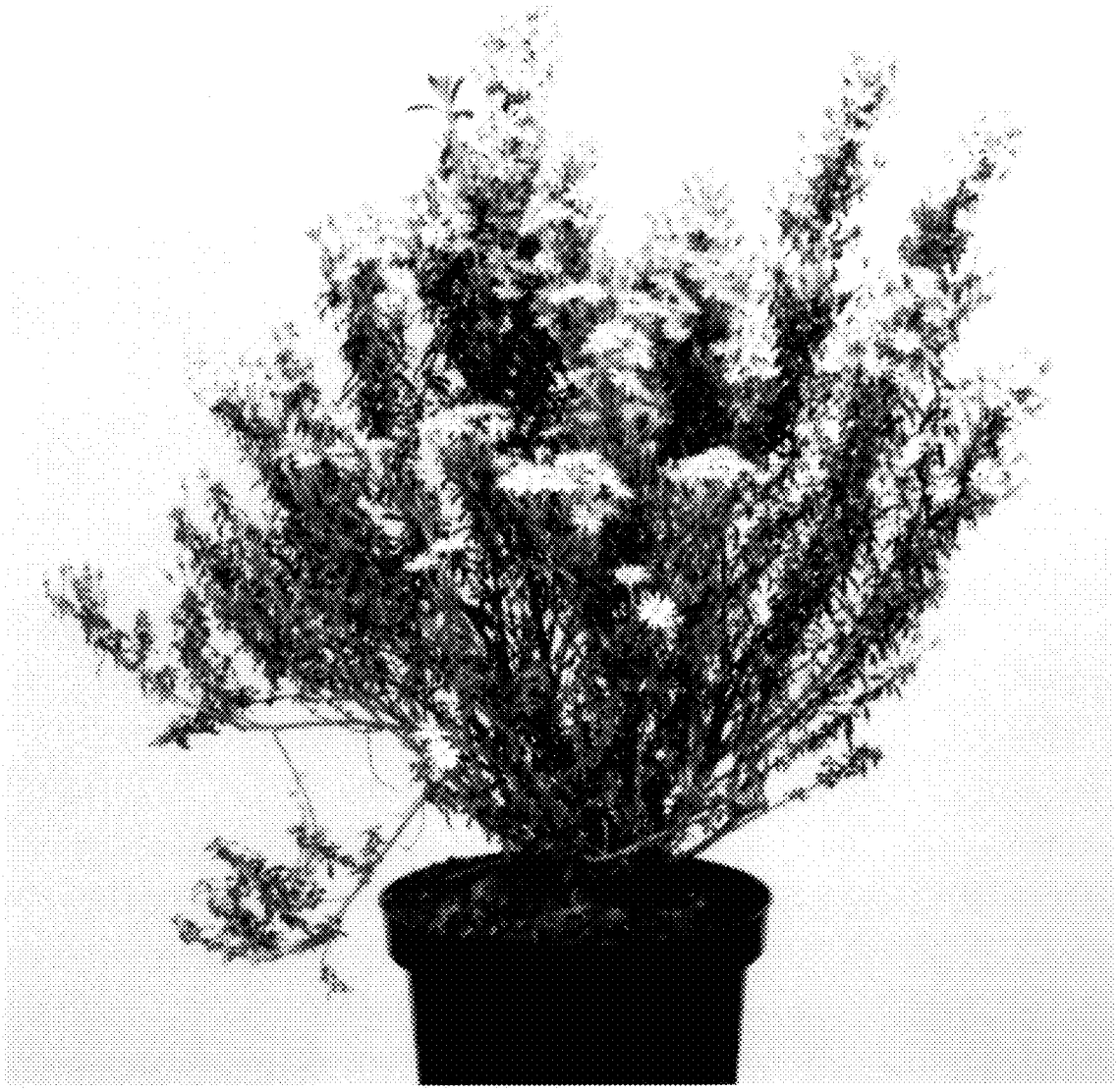
Figure 2:
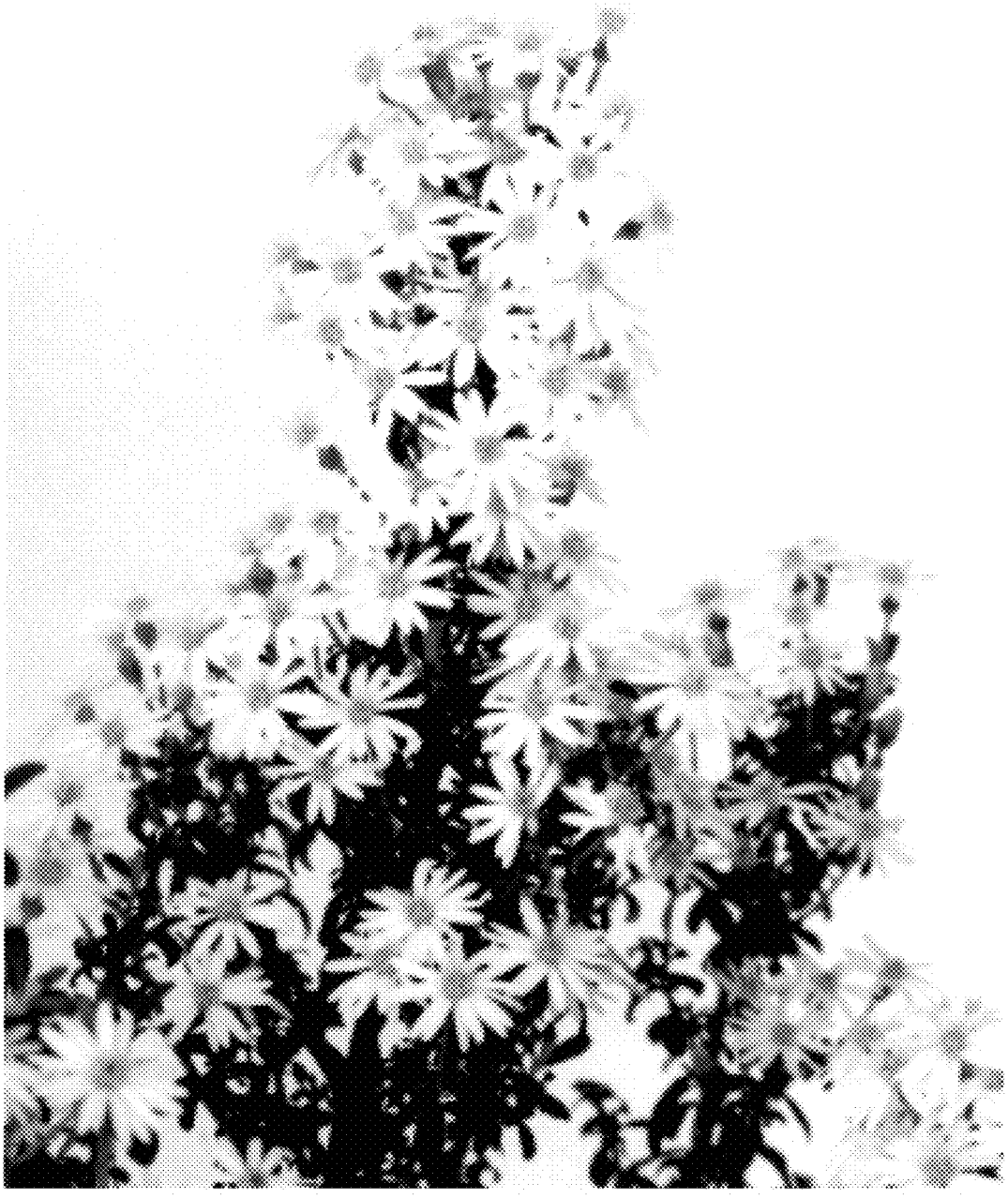

The photograph in FIG. 2 provides a view of the inflorescences of 'ARKPAP'.

Figure 3:
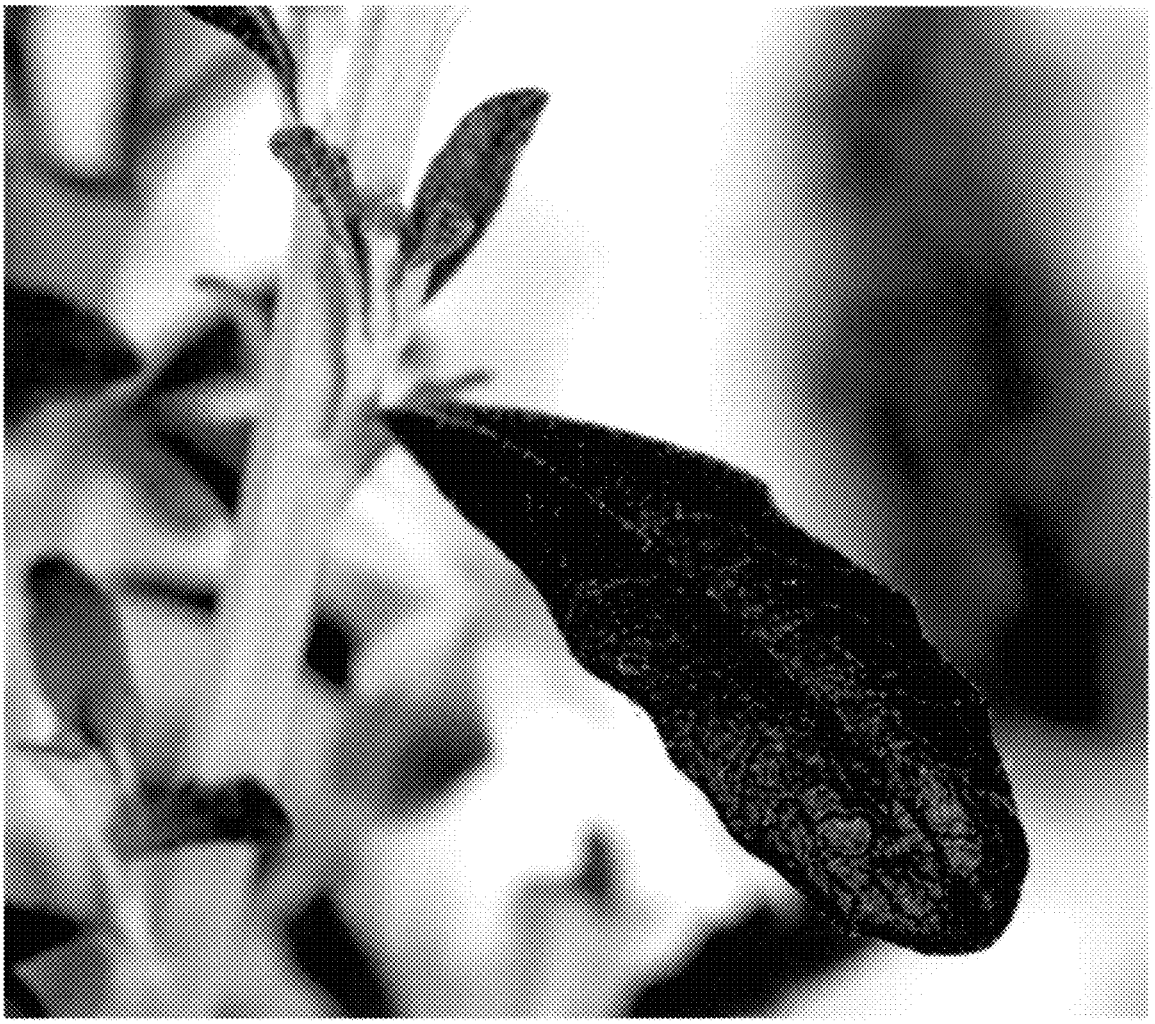

The photograph in FIG. 3 provides a view of a leaf of 'ARKPAP'.

The colors in the photographs are as close as possible with digital photography techniques available, the color values cited in the detailed botanical description accurately describe the colors of the new *Olearia*.

DETAILED BOTANICAL DESCRIPTION

The following is a description of 2-year-old plants of the new cultivar as grown in a greenhouse in 23-cm containers in Essex, The United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming season.*—May to June in The United Kingdom.

*Plant type.*—Evergreen shrub.

*Plant habit.*—Broad obovate to near globular, broadly spreading-upright.

*Height and spread.*—An average of 58.5 cm in height (soil level to top of foliar plane), 60.7 cm in height (soil level to top of floral plane) and 57.3 cm in width as grown in a 23-cm container, reaches 1.5 m in height and 60 cm in width when grown in the landscape.

*Hardiness.*—At least in U.S.D.A. Zones 9 to 11.

*Diseases and pest resistance.*—No susceptibility or resistance to diseases or pests has been observed.

*Root description.*—Fibrous.

*Propagation.*—Stem cuttings.

*Root development.*—3 to 4 weeks for root initiation, 8 to 10 weeks to produce a young plant from a rooted cutting.

*Growth rate.*—Moderate to highly vigorous.

Stem description:

*Stem color.*—Young stems; 193A, mature stems and internodes; 195C to 195D, bark color; 197A and N199A.

*Stem surface.*—Matte, densely covered with very short stellate hairs, an average of 0.1 mm in length, color matches stem surface.

*Stem fragrance.*—Strong musky fragrance.

*Stem strength.*—Moderately strong to strong.

*Stem shape.*—Rounded, slightly pentagonal.

*Stem size.*—Average of 18 cm in length, 2 mm in diameter.

*Branching habit.*—15 main stems with an average of 12 lateral branches per main branch, lateral branches held at an average angle of 30° from main stems.

*Internode length.*—Average of 7 mm.

Foliage description:

*Leaf division.*—Simple.

*Leaf shape.*—Oblanceolate to oblong.

*Leaf base.*—Attenuate.

*Leaf apex.*—Obtuse to bluntly acute.

*Leaf margin.*—Coarsely crenate-dentate, moderately revolute, slightly undulate.

*Leaf venation.*—Pinnate, upper surface 137A, lower surface 195B.

*Leaf attachment.*—Petiolate.

*Leaf arrangement.*—Alternate.

*Leaf number.*—Average of 20 per stem 12 cm in length.

*Leaf surface.*—Upper surface; moderately rugose and moderately glossy, sparsely covered with very short stellate hairs 0.1 mm in length, 195B, lower surface; non-rugose and matte, densely covered with very short stellate hairs; 0.1 mm in length, and 195B in color.

*Leaf color.*—Young upper surface 137A, young lower surface 194B to 194C, mature upper surface NN137B, mature lower surface 195B.

*Leaf size.*—Average of 2.1 cm in length and 5.5 mm in width.

*Leaf fragrance.*—Strong musky fragrance.

*Petioles.*—An average of 1.25 mm in length, 1 mm in width, flattened in shape, both sides matte, medium strength, upper side smooth and glabrous, lower side densely covered with very short stellate hairs; an average of 0.1 mm in length, 195B in color, color upper surface 143A, color lower surface 195B.

Flower description:

*Inflorescence type.*—Axillary, solitary inflorescence.

*Inflorescence shape.*—Rotate, ray florets surrounding disc florets.

*Inflorescence aspect.*—Upward to slightly outward.

*Lastingness of individual capitula.*—Average of 10 days, persistent.

*Flowering habit.*—Very freely flowering.

*Fragrance.*—Strong, sweet and somewhat musky.

*Quantity of capitula.*—Average of 4 per lateral branch and 680 per plant.

*Capitula buds.*—Average of 1 cm in length, 3.5 mm in diameter, oblong in shape, matte surface, 138B, top (immature ray florets) 150C to 150D in color, involucre bracts densely pubescent covered with very small stellate hairs; an average of 0.1 mm in length, 195B to 195C in color.

*Capitula size.*—Average of 1.2 cm in height, 2.3 cm in diameter, disc diameter 8 mm.

*Receptacle.*—Broad deltoid in shape, 0.5 mm in height, 2 mm in diameter, 148C to 148D in color.

*Peduncle.*—Average of 1.9 cm in length, 1 mm in diameter, medium in strength, 143A in color, surface is matte and densely covered with very short stellate hairs an average of 0.1 mm, 195C in color.

*Involucre bracts (phyllaries).*—Rotate, average of 24, 2 rows of whorls, 3 mm in length, 7.5 mm in width, oblong to lanceolate in shape, acute apex, cuneate base, entire margins, upper surface glabrous, glossy, lower surface densely pubescent with very small stellate hairs, 0.1 mm in length, 195B to 195C, color: upper surface; 146B, lower surface 138B, top margins tinged 197A.

*Ray florets.*—Rotate around disc florets, average of 17 (varying between 14 and 19), 1 whorl, lower part tubular and in a 90° angle to wide part of ray floret, implanted into disc, 1.5 cm in length, 2 mm in width, narrow oblong to oblanceolate in shape, flattened, lower 40% tubular, apex acute, fused base, entire margins, upper surface; glabrous, slightly velvety, matte, lower surface; glabrous, moderately velvety, moderately glossy, both surfaces non-rugose, base of tubular part of single whorl of hairs (pappus) is implanted on top of the ovary an average of 4 mm in length, 157A in color, color: when opening and fully open upper and lower surface; lower 40% (tube) 145A, upper 60% NN155D.

*Disc florets.*—Randomly placed on disc, an average of 20, tubular, upright, lower 90% fused into tube, upper 10% free, 9 mm in length, 2.5 mm in width, apices of free lobes acute, reflexed, entire margins, both surfaces glabrous and matte, base of tubular part of single whorl of hairs (pappus) is implanted on top of the ovary an average of 4 mm in length, 157A in color, color: when opening upper and lower surface; 12B, tips N144C, lower half 145B, when fully open upper and lower surface; 150C, lower half 145C, upper surface fading to 195C, lower half 145C.

Reproductive organs:

*Presence.*—Disc florets are perfect, ray florets are pistillate.

*Gynoecium.*—Pistil; 1 per floret, 6 mm in length, stigma; 1 mm in length, cleft, decurrent, 148D in color, style; is 5 mm in length, 147D in color, ovary; 146D in color.

*Androecium.*—Stamens; 5 per floret, anther; linear, 1 mm in length, 0.25 mm in width, 146D in color, filament; 4 mm in length, 145D in color, pollen; low in quantity and 12C in color.

*Fruit and seed.*—None observed to date.

It is claimed:

1. A new and distinct cultivar of *Olearia* plant named 'ARKPAP' as described and illustrated herein.

* * * * *